United States Patent [19]
Koehler et al.

[11] Patent Number: 5,753,708
[45] Date of Patent: May 19, 1998

[54] DERIVATIVES OF 4-HYDROXYBUTYRIC ACID

[76] Inventors: Gernot Koehler; Anita Koehler, both of Hochstrasse 14, 6146 Alsbach, Germany

[21] Appl. No.: 636,681

[22] Filed: Apr. 23, 1996

Related U.S. Application Data

[60] Continuation of Ser. No. 321,009, Oct. 6, 1994, abandoned, which is a division of Ser. No. 958,126, Dec. 29, 1992, Pat. No. 5,380,937.

[30] Foreign Application Priority Data

Apr. 29, 1991 [DE] Germany .................. 41 13 984.4

[51] Int. Cl.$^6$ ............................................. A61K 31/16
[52] U.S. Cl. .................................................... 514/629
[58] Field of Search ..................... 514/629; 564/133, 564/134, 201, 203

[56] References Cited

U.S. PATENT DOCUMENTS

| | | | |
|---|---|---|---|
| 4,143,159 | 3/1979 | Moller et al. ................... | 424/358 |
| 4,227,979 | 10/1980 | Humke et al. ................. | 204/159.16 |
| 4,448,905 | 5/1984 | Lin et al. ...................... | 521/164 |
| 4,549,010 | 10/1985 | Sparer et al. .................. | 528/361 |
| 4,771,074 | 9/1988 | Lammerant et al. ............ | 514/554 |
| 5,506,268 | 4/1996 | Balandrin et al. .............. | 514/629 |

OTHER PUBLICATIONS

CAS Registry Handbook, RN68083-83-0 (1979).

The Merck Index, 11 (1989), Abstract 8603.

*Primary Examiner*—Gary Geist
*Assistant Examiner*—Jean F. Vollano
*Attorney, Agent, or Firm*—Jacobson, Price, Holman & Stern, PLLC

[57] ABSTRACT

The invention describes new salts and amides of 4-hydroxybutyric acid with the aim of improving the pharmacological and therapeutic properties of 4-hydroxybutyric acid.

5 Claims, No Drawings

DERIVATIVES OF 4-HYDROXYBUTYRIC ACID

This application is a continuation of application Ser. No. 08/321,009, filed Oct. 6, 1994, now abandoned, which is a division of application Ser. No. 07/958,126, filed Dec. 29, 1992, now U.S. Pat. No. 5,380,937.

The invention relates to water soluble derivatives of 4-hydroxybutyric acid, processes for their production and their pharmacological use.

4-hydroxybutyric acid or also gamma-hydroxybutyric acid (GHB) has for many years been in general use clinically as a narcotic. This substance is available as a pharmaceutical exclusively as the sodium salt and is approved, for example in Germany, under the trade name SOMSANIT. All experimental and clinical investigations have without exception been performed with the sodium salt of GHB, the acid itself or the corresponding lactone.

In 1950, ROBERTS and FRANKEL detected gamma-aminobutyric acid (GABA) in the mammalian brain. Two years later, FLOREY discovered the inhibitory effect of GABA on the central nervous system which leads to the symptoms of physiological sleep. In 1958, ROBERTS and his collaborators and ALBERS and SALVADOR reported that gamma-aminobutyric acid is reduced in the brain by a specific transaminase into the succinic acid semi-aldehyde which is reduced by a dehydrogenase to GHB.

Parenterally administered gamma-aminobutyric acid cannot cross the blood-brain barrier. LABORIT and collaborators, BESSMAN and FISHBEIN sought derivatives which reach the central nervous system by haematogenous routes. Within the context of these investigations LABORIT, JOUANY, GERARD and FABIAN first reported the narcotic effect of 4-hydroxybutyric acid in 1960.

Quantitative studies by BESSMAN and FISHBEIN into the distribution of GHB and the corresponding gamma-butyrolactone in the organism confirm that GHB is a physiological metabolite of the human brain, where this probably sole metabolite with anaesthetic effects reaches concentrations of up to 0.3 mmol/g.

Pharmacological properties

At a dose of 35 to approximately 90 mg/kg body weight, GHB has a hypnotic effect and at dosages in excess of 100 mg/kg body weight a narcotic effect. Since SOMSANIT has no analgesic effects below 90 mg/kg body weight, it must be combined with analgesics, neuroleptics or with a subliminal barbiturate dose in order to achieve sufficient anaesthesia in surgical interventions. For internal indications on the other hand (e.g. sleep therapy, terminal carcinomatous state), GHB may also be used as a 'sole narcotic'.

A E USPENSKIJ's investigations showed that sodium 4-hydroxybutyrate inhibits the polysynaptic reflexes, while the monosynaptic reflexes remain unchanged, even at dosages of up to 2 g/kg in cats.

Several particular properties which distinguish GHB from other anaesthetics deserve mention: the eyelid reflex disappears, the eyelids slacken, but the eyes often remain half open. The corneal reflex is generally retained. Induction is slow, awakening is relatively rapid. Depending on the dose, the period of activity is 1–2 hours. According to investigations by FISHBEIN and BESSMAN, the narcosis achieved with GHB broadly resembles physiological sleep. In general, respiration becomes deeper with increased amplitude and decreased frequency. The sensitivity of the respiratory centre to carbon dioxide stimulus is retained, GHB does not therefore itself act as a respiratory depressant, but it may possibly potentiate the respiratory depressive effect of other anaesthetics.

In exceptional cases, a typical intermittent respiration occurs for a short period, particularly during the awakening phase. Disturbances of the acid-base balance could not, however, be identified during these phases, normalisation occurred after a short period without therapeutic measures.

An increase in blood pressure is more frequently observed after administration of GHB. In investigations performed to date, it has not been possible to identify any direct depressive effect on the myocardium even when high doses are used. Investigations performed on rats allow a statement to be made concerning the break-down of GHB in the organism. 97% of the marked carbon ($C^{14}$) could be detected within 2 hours as $CO^2$ in the expiratory air.

A final point to be mentioned is that the electrolyte balance is not significantly changed during GHB narcosis. There is merely a shift of potassium from the interstitial fluid to the intracellular fluid. This shift, however, is never of threatening proportions.

Significance of the invention

Regarding the previously observed slight side-effects, attention was always directed towards the specific effect of GHB and the sodium cation was not taken into consideration, as it was classified merely as a physiological charge carrier improving solubility with little clinical value as a galenical component.

With the increasing significance of GHB also in closed cranio-cerebral trauma and in its oral applications for therapy of alcohol withdrawal, of narcolepsy and as a soporific, the side-effects take on greater significance. The critical parameters are outlined with the following keywords:

with i.v. administration:

increase in intracranial pressure electrolyte shift caution: renal insufficiency clonic muscle spasms with oral administration:

nausea flavour diarrhoea compliance

The problem of the invention is therefore further to reduce the side-effects.

To this end, the invention proposes new water-soluble derivatives of 4-hydroxybutyric acid (GHB) with improved clinical and pharmacological properties with the general formulae I and II.

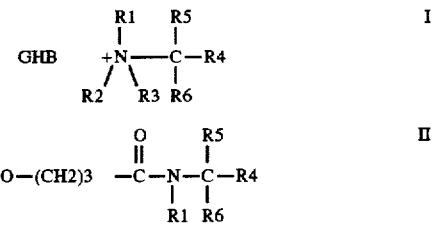

R1, R2 and R3 may mean H—, CH3—, C2H5—, CH2OH—CH2— or CH2OH—CHOH—CH2— groups or may form with nitrogen a heterocycloalkane with 4 or 5 carbon atoms.

R4 is an alcohol or polyalcohol with 1 to 5 carbon atoms and 1 to 5 oxygen atoms of linear, branched or cyclic structure. R1 and R4 may also be condensed with each other to a cyclic ether. (Morpholine and derivatives) R5 and R6 may mutually independently be H— or CH2OH—.

The compounds according to the invention are suitable, by way of example to increase further the effectiveness of antibiotics.

Preferred examples of the salts according to the invention are given in claims 2 to 8. Preferred examples of the amides according to the invention are named in claims 9 to 14.

To produce the salts according to the invention, an amino polyalcohol of the stated type is added to an aqueous solution of gamma-butyrolactone, the aqueous solution is gently heated until its Ph value is adjusted to approximately 7.5 and the volume of the solution obtained is then adjusted to the desired concentration of 4-hydroxybutyric acid by the addition of water.

To produce the amides of gamma-hydroxybutyric acid, gamma-butyrolactone is reacted together with a primary or secondary amino alcohol or a morpholine derivative in a suitable solvent, preferably a lower alcohol at temperatures between 40° C. and 120° C. Once the solvent has been distilled off, the desired amide is obtained.

The aqueous solutions obtained of the salts and/or amides according to the invention are effective as parenteral preparations for narcosis in anaesthesia, for sleep induction and in long-term sedation and may successfully be used as oral preparations in therapy for alcohol withdrawal, cataplexy, narcolepsy or sleep disturbance syndrome. The side-effects mentioned above attributed to the sodium in the sodium salt of GHB substantially no longer occur in the pharmacological use of the butyric acid derivatives according to the invention.

EXAMPLE 1

1-desoxy-1-methylamino-D-glucitol 4-hydroxybutyrate 500 ml (565 g, 6.56 mol) of gamma-butyrolactone are placed in 1.8 l of water. 1.28 kg (6.56 mol) of methylglucamine are added to the solution obtained. The mixture is then heated to 60° C. for 8 hours. The pH value falls over this period from an initial value of 11 to 7.5. The volume of the solution obtained is then adjusted to 3.4 l by the addition of water (approximately 200 ml) in order to achieve a concentration of 2 g of gamma-hydroxybutyric acid in 10 ml of solution.

EXAMPLE 2

Trishydroxymethyl-aminomethane 4-hydroxybutyrate 500 ml (565 g, 6.56 mol) of gamma-butyrolactone are placed in 1.8 l of water. 795 g (6.56 mol) of trishydroxymethylmethylamine are added to the solution obtained. The mixture is then heated to 60° C. for 8 hours. The pH value falls over this period from an initial value of 10.5 to 7.5. The volume of the solution obtained is then adjusted to 3.4 l by the addition of water in order to achieve a concentration of 2 g of gamma-hydroxybutyric acid in 10 ml of solution.

EXAMPLE 3

1-desoxy-1-(N-4-hydroxybutyroyl-N-methylamino)-D-glucitol 500 ml (565 g, 6.56 mol) of gamma-butyrolactone are placed in 2.0 l of methanol. 1.28 kg (6.56 mol) of methylglucamine are added to the solution obtained. The mixture is then refluxed for 16 hours. The solution obtained is evaporated to dryness. The colourless syrup so initially obtained crystallises into a white solid after a few days at room temperature. (Melting point 78°–79° C.)

EXAMPLE 4

N-(2-hydroxyethyl)-4-hydroxybutyramide

A solution of 61 g of ethanolamine in 70 ml of methanol is added dropwise to a solution of 88 g of gamma-butyrolactone in 120 ml. The mixture is refluxed for 8 hours and then evaporated to dryness. The viscous oil obtained crystallises after standing for some time. The substance is recrystallised from acetone and vacuum dried. (White solid, melting point 55°–56° C.)

We claim:

1. A parenteral preparation for narcosis in anaesthesia consisting essentially of an aqueous solution of at least one compound selected from the group consisting of N-2-hydroxyethyl-4-hydroxybutyramide, N-2-hydroxyethyl-N-methyl-4-hydroxybutyramide, N,N-bis-(2-hydroxyethyl)-4-hydroxybutyramide and N-(1-hydroxymethyl-2-hydroxyethyl)-4-hydroxybutyramide.

2. A parenteral preparation for sleep induction or long-term sedation consisting essentially of an aqueous solution of at least one compound selected from the group consisting of N-2-hydroxyethyl-4-hydroxybutyramide, N-2-hydroxyethyl-N-methyl-4-hydroxybutyramide, N,N-bis-(2-hydroxyethyl)-4-hydroxybutyramide and N-(1-hydroxymethyl-2-hydroxyethyl)-4-hydroxybutyramide.

3. An oral preparation for alcohol withdrawal therapy consisting essentially of at least one compound selected from the group consisting of N-2-hydroxyethyl-4-hydroxybutyramide, N-2-hydroxyethyl-N-methyl-4-hydroxybutyramide, N,N-bis-(2-hydroxyethyl)-4-hydroxybutyramide and N-(1-hydroxymethyl-2-hydroxyethyl)-4-hydroxybutyramide and a pharmaceutically effective carrier.

4. An oral preparation for therapy of cataplexy or narcolepsy consisting essentially of at least one compound selected from the group consisting of N-2-hydroxyethyl-4-hydroxybutyramide, N-2-hydroxyethyl-N-methyl-4-hydroxybutyramide, N,N-bis-(2-hydroxyethyl)-4-hydroxybutyramide and N-(1-hydroxymethyl-2-hydroxyethyl)-4-hydroxybutyramide and a pharmaceutically effective carrier.

5. An oral preparation for therapy of sleep disturbance syndrome consisting essentially of comprising at least one compound selected from the group consisting of N-2-hydroxyethyl-4-hydroxybutyramide, N-2-hydroxyethyl-N-methyl-4-hydroxybutyramide, N,N-bis-(2-hydroxyethyl)-4-hydroxybutyramide and N-(1-hydroxymethyl-2-hydroxyethyl)-4-hydroxybutyramide and a pharmaceutically effective carrier.

* * * * *